United States Patent [19]

Kitagawa et al.

[11] Patent Number: 4,743,250
[45] Date of Patent: May 10, 1988

[54] ARTIFICIAL BLOOD VESSEL AND METHOD OF MANUFACTURE

[75] Inventors: Hideaki Kitagawa, Kyoto; Koji Watanabe, Otsu; Miyoshi Okamoto, Takatsuki, all of Japan

[73] Assignee: Toray Industries, Inc., Tokyo, Japan

[21] Appl. No.: 785,662

[22] Filed: Oct. 9, 1985

[30] Foreign Application Priority Data

Oct. 15, 1984 [JP] Japan ................................ 59-214410

[51] Int. Cl.$^4$ ................................................ A61F 2/06
[52] U.S. Cl. ............................................ 623/1; 623/66
[58] Field of Search ................. 623/1, 12, 66; 156/72; 428/91, 904; 26/2 R; 28/159, 160, 271

[56] References Cited

U.S. PATENT DOCUMENTS

| 3,751,777 | 8/1973 | Turmel et al. | 28/159 |
| 4,136,221 | 1/1979 | Okamoto et al. | 28/159 X |
| 4,164,045 | 8/1979 | Bokros et al. | 623/1 |
| 4,193,137 | 3/1980 | Heck | 623/1 |
| 4,303,706 | 12/1981 | Minemura et al. | 156/72 X |
| 4,318,949 | 3/1982 | Okamoto et al. | 156/72 X |
| 4,377,010 | 3/1983 | Fydelor et al. | 623/12 X |
| 4,445,903 | 5/1984 | Minemura et al. | 8/492 |
| 4,497,095 | 2/1985 | Minemura et al. | 26/2 R |
| 4,548,628 | 10/1985 | Miyake et al. | 55/487 |
| 4,596,577 | 6/1986 | Sato | 428/91 X |
| 4,612,228 | 9/1986 | Kato et al. | 428/904 X |
| 4,695,280 | 9/1987 | Watanabe et al. | 623/1 |

FOREIGN PATENT DOCUMENTS

A0011437 5/1980 European Pat. Off. ............ 623/1 X

Primary Examiner—Richard J. Apley
Assistant Examiner—Alan W. Cannon
Attorney, Agent, or Firm—Cushman, Darby & Cushman

[57] ABSTRACT

An artificial blood vessel comprises a woven, braided or knitted fabric structure. Fibers so extend from a surface of the fabric structure as to be randomly intertwined with the fabric structure. The intertwining of the fibers with the fabric structure can be achieved by applying a high fluid pressure against a surface of the fabric structure.

4 Claims, 2 Drawing Sheets

ARTIFICIAL BLOOD VESSEL AND METHOD OF MANUFACTURE

BACKGROUND OF THE INVENTION

This invention relates to an artificial blood vessels which are highly fray-resistant and antithrombic and which provide excellent inosculation, and to a method of manufacturing such artificial blood vessels.

DESCRIPTION OF THE PRIOR ART

Conventional artificial blood vessels consist of a woven or knitted fabric made up of polyester fibers, and may be provided on both faces thereof with pile loops to facilitate growth of tissue from one face to the other (see U.S. Pat. No. 4193137). In order to prevent the leakage of blood through the walls of such artificial blood vessels the structure must have an extremely high density; or in other words, it must be a tightly woven/knitted fabric.

Artificial blood vessels constructed of woven fabric are especially difficult to pass a needle through during an operation and inosculation with the body's natural blood vessels is extremely difficult, thus forcing a heavy burden upon the doctor performing the operation. In addition, the extremely simple structure of woven blood vessels has, in the past, made it easy for them to fray after the suture needle had been passed through the fabric or when they were joined to the body's natural blood vessels, thus resulting in imperfect inosculation. In order to improve the fray-resistance and the needle passage, an extremely complex woven/knitted structure was used. Thus, because it was necessary to construct a complex knitted structure, the thread used necessarily had to be extremely thin and the knitting machine had to be a specially made high-precision model.

SUMMARY OF THE INVENTION

This invention provides the following:

1. An artificial blood vessel comprising a woven, braided or knitted fabric structure, the blood vessel further comprising fibers so extending from a surface of the woven, braided or knitted fabric structure as to be randomly intertwined with the said fabric structure.

2. A method of manufacturing an artificial blood vessel of fabric having a woven, braided or knitted structure wherein, by applying a high fluid pressure against a surface of the said fabric structure, fibers on the said surface are randomly intertwined with the said fabric structure.

DESCRIPTION OF THE PREFERRED EMBODIMENTS

Figure 1:
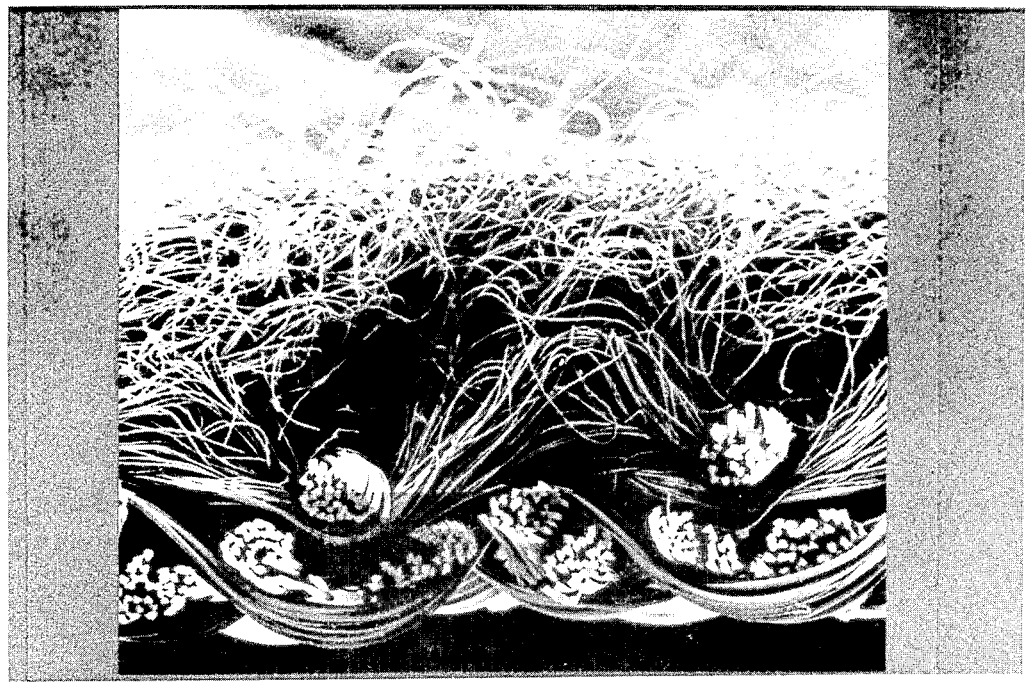
FIG. 1 is a photomicrograph of a section through a woven fabric structure having a nap on a surface thereof prior to treatment with a high pressure fluid.

The fibers on the surface of the woven, braided or knitted fabric structure may be provided by forming a nap on a surface of the fabric structure. The nap fibers are not, therefore, woven, braided or knitted throughout their entire lengths into the fabric structure but are free to intertwine with the fabric structure on being subjected to the high pressure treatment. The nap may be defined by at least one of shag and loop fibers.

Alternatively, the fibers on the surface of the woven, braided or knitted fabric structure may be provided by loose fibers deposited on to the surface of the fabric structure or by a non-woven fabric laid or lightly woven on to the woven, braided or knitted fabric structure and having fibers therein free to intertwine with the structure on application of the high fluid pressure.

The high pressure fluid treatment may be applied against a surface of the fabric structure either before or subsequent to its assuming the tubular form for use as a blood vessel. In any event it is preferred to apply the high pressure fluid when the fabric structure is in tubular form, more preferably before turning it inside out into a form in which it will be used as an artificial blood vessel.

Where a nap is formed on the surface of the fabric structure, this nap formation may be achieved as a result of the high fluid pressure treatment which then serves both to form the nap and cause fibers thereof to intertwine with the fabric structure. In such a case, the nap may extend inwardly rather than outwardly of the fabric structure at the surface to which the high fluid pressure is applied, but may extend outwardly from the opposite surface.

However, it is preferred to form the nap on the fabric structure prior to application of the high fluid pressure.

The high fluid pressure treatment is preferably carried out by directing a jet of fluid at a surface of the woven, braided or knitted fabric structure, more preferably at a nap on the said fabric surface.

With this invention, the basic structure can be a woven fabric, a knitted fabric, or braided. The structure may be constructed either from a yarn of single fiber component or a yarn containing two or more fiber components such as mixed or parallel-arrayed fiber yarns. In addition, the basic structure can constitute one type of yarn, or alternatively it can constitute two or more types of yarn.

Although performance of the invention does not require the use of a particular type of fiber, examples of useful fibers are those of polyester, polyamide, polytetrafluroethylene and polyolefin, of which polyester is best. It is also possible to use a multicomponent fiber from which one component is later removed to obtain superfine fibers. The final, remaining polymer is preferably one of those mentioned above, while the polymers to be removed is suitably polystyrene, polyethylene, a water-soluble polyamide, polyester soluble in an aqueous alkaline solution, or a water-soluble polyvinyl alcohol.

In order to make this invention more effective, it is best if at least some of the fibers used to make up the structure are superfine fibers with a single-fiber thickness (i.e. fineness) of 1 denier or less. By using superfine fiber, not only can the three-dimensional intertwining achieved by the high-pressure fluid processing (which will be discussed later) be increased, but in addition extremely pliable artificial blood vessels of low porosity, and which therefore exhibit low blood leakage, can be produced.

In addition, the use of superfine fiber makes the gaps between fibers extremely small and numerous, which makes it easy for cells to enter and fill the gaps. Thus the fibrin precipitation become extremely thin, uniform, and firm.

On the other hand, however, with such superfine fibers, there are the problems associated with the weakening of the fibers while in the body and their possible absorption or disappearance (possibly due to a hydrolysis reaction which occurs in the body). The thinner the fibers the faster the weakening.

Thus, in order to both take advantage of the special characteristics of superfine fibers and yet avoid the abovementioned problems therewith, it is best to construct the artificial blood vessels by intertwining superfine fiber A measuring 1.0 denier or less (or even better, 0.5 denier or less) and fiber B measuring more than 1.0 denier (or even better, more than 1.5 denier). The fiber A is most preferably ultrafine fiber, especially fiber having a fineness of 0.2 denier or less. The fiber B suppresses the weakening of the structure in the body and superfine fiber A improves the formation of shag and/or loops which helps the intertwining, the acceptance by the living body, the pliancy, the intertwineability, and the ease with which a needle can pass through the artificial blood vessel.

Note that although the fiber used in this invention can be either filament yarn or staple yarn, filament yarn has the advantage of allowing the wall thickness of the artificial blood vessels to be freely adjusted.

In addition, the presence of shag and/or loops in artificial blood vessels improves the formation of new living intima, and it is especially good to have shag and/or loops of superfine, especially ultrafine fibers. In addition, the presence of shag and/or loops helps to increase the adhesion of the outer walls to the surrounding tissue, and this is another objective achieve by this invention.

In addition, concerning the aforementioned superfine fibers, although it is possible to use fibers which are already superfine, it is also possible to construct the tube of fibers which, after formation of the tube, can be made superfine by either chemical or physical means. Although superfine fiber can be obtained through very careful use of a conventional spinning process, it is also possible to make fibers such as polyester superfine by drawing the undrawn thread under specified conditions.

Fibers which can be made superfine through a subsequent process refers to multicomponent fibers from each of which can be obtained a plurality of super fine fibers, i.e. fibrils, by processes such as removing one of the components or by peeling the components apart from one another, as can be seen in JP-B-22126/73. Because the use of such fibers makes it possible to use a normal fiber thickness when constructing the tube and then later make the fibers superfine, such problems as fiber breakage or fluff formation during processing of the fiber prior to or during weaving, knitting or braiding can be minimized.

In any case, in this invention, at least part of the aforementioned shag and/or loop shaped fibers must be intertwined with the fibers which make up the basic structure. The resulting structure provides artificial blood vessels which are highly fray-resistant and antithrombic and which provides excellent inosculation.

Although it is possible by the high pressure fluid treatment simultaneously to form a nap and cause intertwining of the nap fibers within the fabric structure, it is preferable to form the nap fibers, which may be shag and/or loops, in the fabric prior to the application of the high-pressure fluid.

One way of forming the shag and/or loops is to do it when constructing the basic structure so as to make the subsequent high-pressure fluid treatment more effective. However, the presence of nap fibers prior to the application of the high fluid pressure is not absolutely necessary. Some kinds of fabric structure which has no nap prior to the high fluid pressure treatment are useful for the method of this invention. For example, superfine fibers in the fabric may be easily formed into fluff and/or loops by high pressure treatment and then intertwined with the fibers of the basic structure. Similarly, relatively loose structure, such as satin weave and twill weave are also can be effectively intertwined by high-pressure fluid jet. As a matter of course, the combination of the superfine fibers and the loose structure makes the effects larger. A typical example of this method is to use pile or cut-pile woven/knit fabric, and loops of varying fiber lengths created by the inclusion of a structure consisting of various fiber lengths or consisting of fibers of essentially the same length as one another but which shrink by varying amounts when subjected to a heat treatment or chemical treatment.

An alternative method of forming a nap is to raise the nap from the fabric structure weaving, braiding or knitting. A typical example of this method is to use a nap-raising machine, or sometimes to even scrape the fabric with sandpaper.

However, the important point of this invention is not which of these methods is used, but the fact that the fibers are present on the surface of the woven, braided or knitted fabric structure which are free to intertwine on subjecting it to the high-pressure fluid treatment. In some cases it is better if the nap is formed on both the inner and outer walls.

Although several methods can be considered for the high-pressure fluid interwining process, using liquid is the most effective and the water jet method is the best in terms of safety and economy. In other words, the best method is to apply a jet of water to a surface of a fabric structure from which extends shag and/or loops (in some cases both sides will have shag and/or loops) and/or to a fabric surface opposite to that from which the shag and/or loops extend using a water jet issuing from small openings at a pressure of 5 to 200 $kg/cm^2$. If the jet pressure is too low, the fibers will not become intertwined; however, if the jet pressure is too high, the fibers will be cut. Thus the pressure is determined within the aforementioned range, for example, according to the strength of the fibers, the thickness of the fibers and the pliancy of the artificial blood vessels.

In addition, there are two possible methods of high-pressure fluid treatment. One is to apply a jet of fluid to the artificial blood vessel from a circular array nozzles which is wider than the artificial blood vessel and which has many tiny openings facing the fabric structure. The other method is to fold the tube-shaped artificial blood vessel flat and direct jet of high pressure fluid on to it from many tiny openings disposed parallel or perpendicular to the axis of the tube. When doing this, it is recommended to insert into the tube a flat or tube-shaped net, plate or bar of plastic, metal, glass, or sometimes foam which may or may not be pervious to water to prevent the inner walls of the tube from sticking to each other. This will also make subsequent processing easier and can sometimes be used to control the diameter of the tube.

High-pressure fluid applicable in this invention may be gas or liquid such as air, steam, water, other inorganic liquid and organic liquid. However water or aqueous solution is the best in practical use in view of safety and economy.

In addition, during the processing of the fabric using the high-fluid fluid jet, it is preferred to oscillate the jet nozzle left and right or cyclicly so that it does not match the pitch of the basic structure. Doing this will reduce the occurrence of heavy traces of the jet. However, in some cases, the oscillating is not necessary.

Turning the tube inside out and performing the high-pressure fluid processing for the inside will increase the fray resistance, but this is not absolutely necessary.

As to forming a fabric into a tube in order to construct the artificial blood vessels, and although it is possible to make the fabric, cut it, and then form the tube by sewing, adhesion, or bonding, it is better to construct the basic structure in the shape of a tube from the beginning because then there is no seam. Note that with the former method (first making a sheet of fabric and then forming it into a tube), the previously mentioned nap-raising work can of course be carried out either while the fabric is still a sheet or after it has been formed into a tube.

As described above, several problems which has proved impossible to solve using conventional technology have been simultaneously eliminated by these newly discovered artificial blood vessels and the method of manufacturing them. The following are the effects of this invertion.

(1) The fray-resistance can be remarkably improved.
(2) The pliability can be improved.
(3) Easy passage of a needle through the vessel is possible, making it easy to sew and preventing damage of the structure should it be necessary to pass a needle through it for injecting fluid into it.
(4) Excellent formation of new living intima can be achieved.
(5) Because the intertwining may be carried out subsequent to construction of the tubular fabric, the base structure can be either simple or complex as needed.
(6) Loose fibers resulting from the nap-raising treatment can be substantially eliminated through washing or re-intertwining.

The invention will now be described in more detail with the reference to the accompanying drawings and the following examples.

EXAMPLE 1

We wove a tube with a quadruple weft and double warp structure so as to form a tube with a front weave of 5-satin structure and back weave of 3/2 twill structure. We used a 50-denier, 24-filament polyethylene terephthalate false-twisted yarn for the warp and the back weft yarn, and for the front weft yarn, a 245-denier, 40-filament multifilaments yarn of islands-in-sea type having 36 islands consisting of 78 parts of polyethylene terephthalate for the islands component and 22 parts of polystyrene for the sea component. The tube was 19 mm in diameter and 100 cm long. We washed it in hot water, dried it, and then used perchloroethylene to remove the polystyrene. The thickness of the resultant superfine fibers was 0.13 denier. Next, we treated the tube with a lubricant to facilitate nap-raising and then raised the nap mechanically (with card clothing raising machine). The structure of the resultant tubular fabric is illustrated by the photomicrograph (magnification is $\times 106$) of FIG. 1. We then treated the tube with a water jet punch using a nozzle having row of jet openings 0.25 mm in diameter spaced 2.5 mm apart at a pressure of 70 kg/cm$^2$. The basic structure of the resulting artificial blood vessel was a double weft structure, but many superfine fibers could be observed intertwined with the woven texture, and with the fiber bundles. We cut this artificial blood vessel with scissors at a 45° angle and checked the cut end for fraying. The results were much better than those obtained with an artificial blood vessel which had not been given the water jet treatment, with virtually no fraying observed in the treated artificial blood vessel. In addition, shag and loops were present on both the inner and outer walls of the tube.

Next the artificial blood vessel was turned inner wall out and outer wall in, crimped (to form a bellows-like construction), heat set, washed with hot water, dried and sterilized with ethylene oxide gas.

Figure 2:
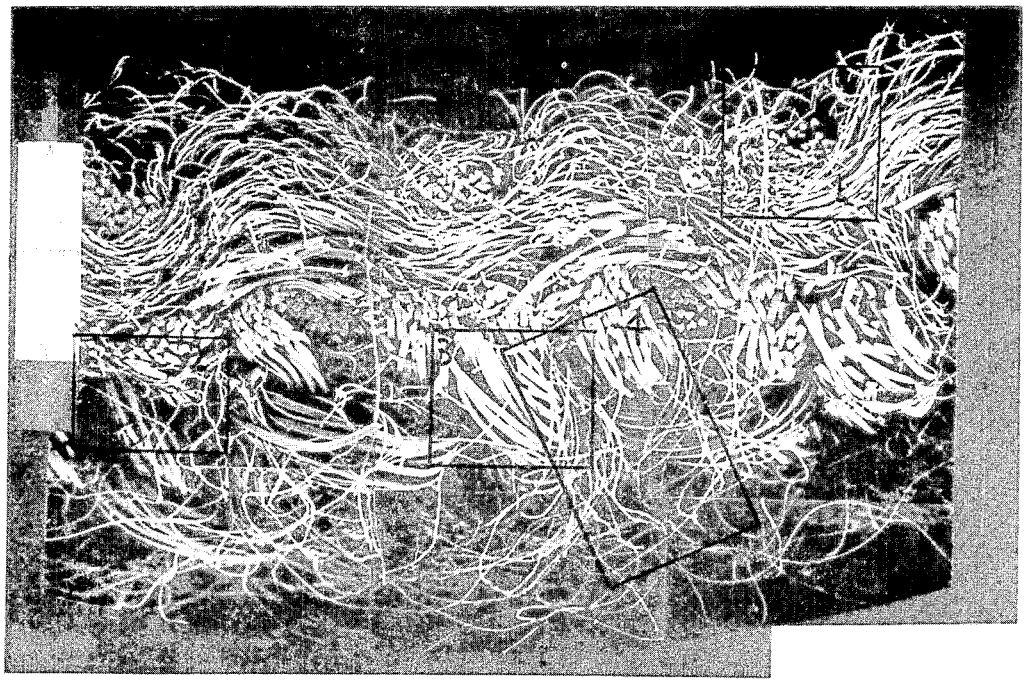
FIG. 2 is a photomicrograph of a section through the fabric structure of FIG. 1, but after treatment with a high pressure fluid.
Figure 3A:
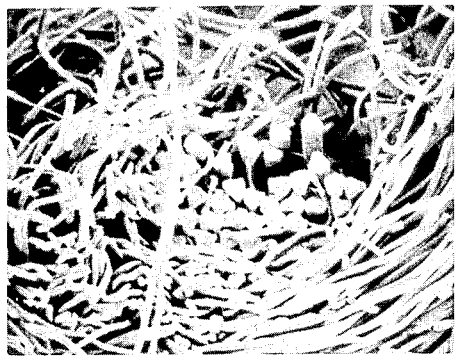
FIGS. 3A-D are enlarged photomicrographs of respective regions of the photomicrograph of FIG. 2 numbered 1-4.
Figure 3B:
Figure 3D:
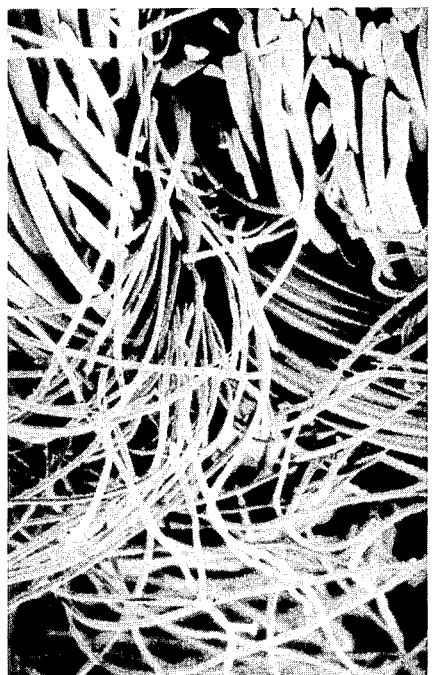
Figure 3C:

The structure of the resultant fabric is illustrated by the photomicrograph (magnification is $\times 106$) of FIG. 2. Each of regions 1–3 (shown in more detail in FIGS. 3A–C respectively; magnification is $\times 300$) contains a section through a respective warp yarn around which are randomly intertwined ultrafine fibers. Region 1 contains a warp section of the front weave essentially at a surface of the fabric, which surface preferably provides the internal periphery of the blood vessel. Regions 2 and 3 contain respective warp sections of the back weave essentially at a surface of the fabric which preferably provides the external periphery of the blood vessel. Region 4 (shown in more detail in FIG. 3D) contains a part of a section of a warp of a back weave structure at the external periphery of the blood vessel and additionally contains randomly intertwined fibers which extend through the fabric and past the warp so as to protrude from the external periphery of the blood vessel.

The water flow rate through the wall of this artificial blood vessel under 120 mmH$_g$ pressure was 180 ml/min. This artificial blood vessel was implanted in place of the descending aorta of a dog. At the implantation, fraying of the artificial blood vessel around both cut portions was not observed during sewing with a living cut aorta of the dog, even though the sewing thread was often pulled. Further the operation was conducted smoothly because the artificial blood vessel show excellent pliancy and inosculation and allow easy passage of a sewing thread through it. Though a pre-clotting test was not carried out because water flow rate through the wall was low, almost no leakage of the blood was observed. However the artificial blood vessel was changed red by migration of the blood through the wall. The result of the observation of the implanted artificial vessel was as follows. After three days, the red color of the artificial blood vessel just after the implantation was reduced and turned light. After 21 days, the migration of the blood decreased and active formation of neo intima was observed. After 3 months, neo intima almost covered the wall, turning it into a glossy light gray color. This means the necessary term for remedy was drastically shortened.

EXAMPLE 2

The artificial blood vessel constructed in Example 1 was turned inside out and the water jet punch treatment was repeated under the same conditions. Not only was the fraying resistance improved, but the shag and/or loops were more uniform than in Example 1.

EXAMPLE 3

We formed a tube 20 mm in diameter with a half structure on a two-needle 30G double-raschel machine using 50-denier, 18-filament and 50-denier, 72-filament (thickness of each filament was 0.69 denier) polyester fibers. We washed the tube in boiling water, dried it, and then raised the nap. Observation of the fabric after the nap was raised revealed that the thinner fiber provided more nap and formed more shag and loops than the thicker one. We then treated the tube with a water jet punch using a nozzle having row of openings 0.3 mm in diameter and spaced 2.5 mm apart at a pressure of 75 kg/cm$^2$. Observation of the resulting artificial blood vessel showed the thinner fibers to be intertwined with the thicker ones among the individual fibers, among the woven texture, and among the fiber bundles. In addition, although relatively few, some of the thicker fibers were also observed to be intertwined among themselves and or intertwined among the thinner fibers. In addition, it was also observed that those fibers were shaped as shag and/or loops and that the shag and/or loops and/or the fibers intertwined with them penetrated through to the inner walls of the tube. This means that this artificial blood vessel may be used withour turning inside out. As a result of checking the fray-resistance of this artificial blood vessel, it was found that it was much better than that of an artificial blood vessel which had not been subjected to water jet treatment, with virtually no fraying. The fray-resistance was especially good at the end of the weave.

We claim:

1. A method of manufacturing an artificial blood vessel of fabric having a woven, braided or knitted fabric structure which comprises forming the fabric into the shape of a tube, inserting a spacer into the tube, and applying a high fluid pressure uniformlly against a surface of the said tube-shaped fabric structure with the spacer inserted therin, the application of the fluid pressure being such that fibers on the said surface are randomly intertwined with said fabric structure.

2. A method as defined in claim 1, wherein at least some of the said intertwined fibers have a fineness less than 1.0 denier.

3. A method as defined in claim 1, wherein the fluid is water.

4. A method as defined in claim 1, wherein fibers extending from a surface of the said fabric structure are provided prior to the said application of the high fluid pressure so as to randomly intertwine the said extending fibers with the fabric structure.

* * * * *